United States Patent
Wang-Lee

(10) Patent No.: US 6,961,959 B2
(45) Date of Patent: Nov. 8, 2005

(54) PROTECTIVE MASK

(75) Inventor: Anthony Wang-Lee, No. 473, Jong-Shan S. Rd., Yung-Kang City, Tainan Hsien (TW)

(73) Assignee: Anthony Wang-Lee, Tainan Hsien (TW)

( * ) Notice: Subject to any disclaimer, the term of this patent is extended or adjusted under 35 U.S.C. 154(b) by 199 days.

(21) Appl. No.: 10/384,881

(22) Filed: Mar. 10, 2003

(65) Prior Publication Data

US 2004/0177426 A1 Sep. 16, 2004

(51) Int. Cl.$^7$ ................................................ A42B 3/18
(52) U.S. Cl. ........................................................ 2/6.3
(58) Field of Search ............................................. 2/6.3

(56) References Cited

U.S. PATENT DOCUMENTS

| | | | | |
|---|---|---|---|---|
| 5,062,156 A | * | 11/1991 | Siegal | 2/8 |
| 5,533,206 A | * | 7/1996 | Petrie et al. | 2/8 |
| 6,151,711 A | * | 11/2000 | Edwards | 2/8 |
| 6,401,244 B1 | * | 6/2002 | Kramer et al. | 2/8 |
| 6,557,174 B2 | * | 5/2003 | Martin et al. | 2/8 |

* cited by examiner

*Primary Examiner*—Katherine M. Moran
(74) *Attorney, Agent, or Firm*—The Webb Law Firm

(57) ABSTRACT

A protective mask includes a mask body made from an anti-infrared plastic material and formed with a window frame. The window frame defines a window. A viewing member is mounted detachably in the window frame so as to cover the window, and permits vision therethrough.

5 Claims, 7 Drawing Sheets

PROTECTIVE MASK

BACKGROUND OF THE INVENTION

1. Field of the Invention

The invention relates to a protective mask, more particularly to a protective mask including a mask body defining a window, and a viewing member mounted detachably on the mask body so as to cover the window.

2. Description of the Related Art

Referring to FIG. 1, a conventional protective mask 1 is shown to be mounted on a helmet 10, and includes a mask body 11 having a front part 111 defining a front window 113, and a flat viewing member 12, such as a tinted glass, mounted securely to the front part 111 so as to cover the front window 113 and so as to attenuate light radiation passing therethrough.

There are many grades of tinted glass that allow attenuation of light radiation to a greater or lesser extent. Since the viewing member 12 is fixed to the mask body 11, replacement of the viewing member 12 according to the actual working situation is not possible.

SUMMARY OF THE INVENTION

Therefore, the object of this invention is to provide a protective mask that can overcome the aforementioned disadvantage associated with the conventional protective mask.

Accordingly, a protective mask of the present invention includes a mask body and a viewing member. The mask body is made from an anti-infrared plastic material, and is formed with a window frame protruding therefrom in a transverse direction relative to the mask body. The window frame defines a window. The viewing member is mounted detachably in the window frame so as to cover the window, and is adapted to permit vision therethrough.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENTS

Figure 1:
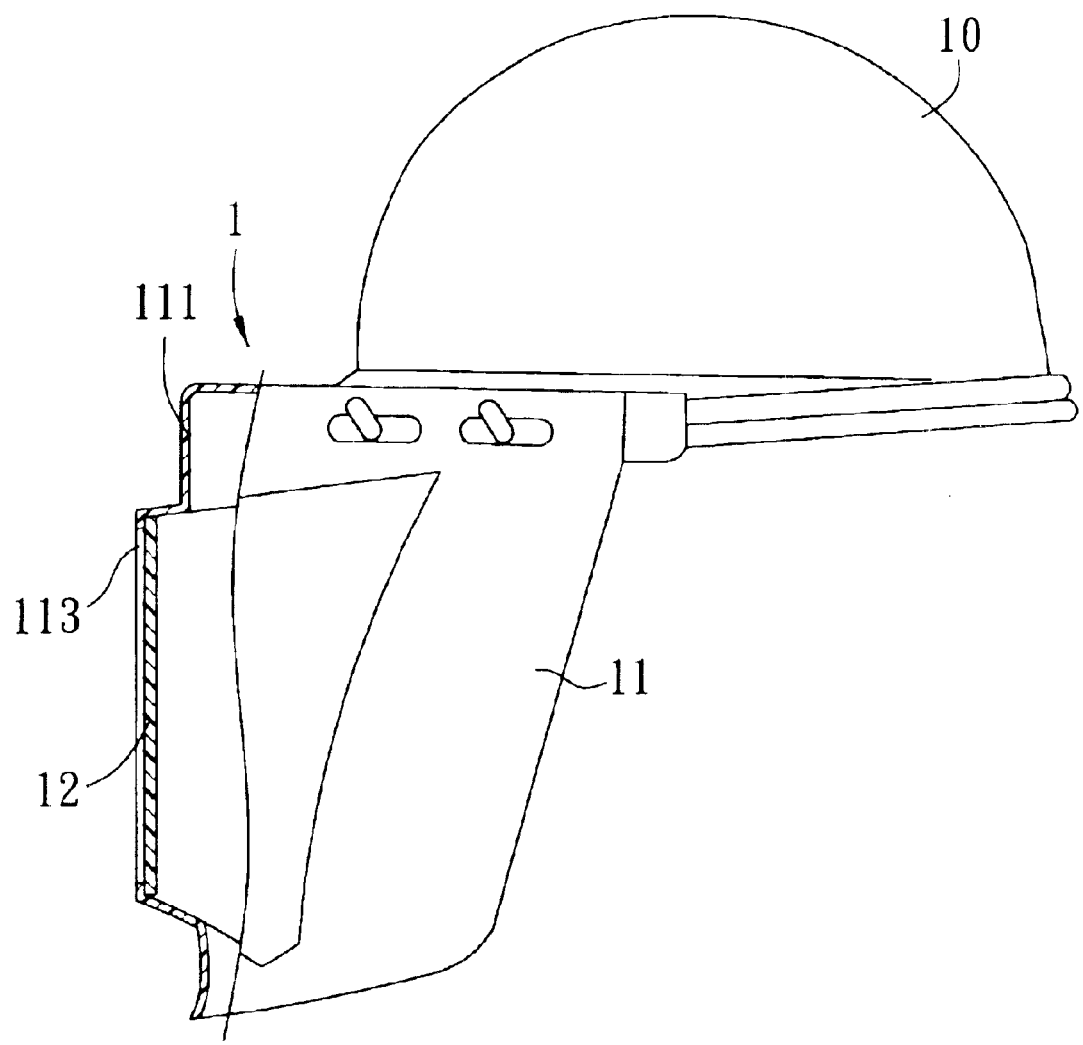
FIG. 1 is a fragmentary sectional view of a conventional protective mask when mounted on a helmet.
Figure 2:
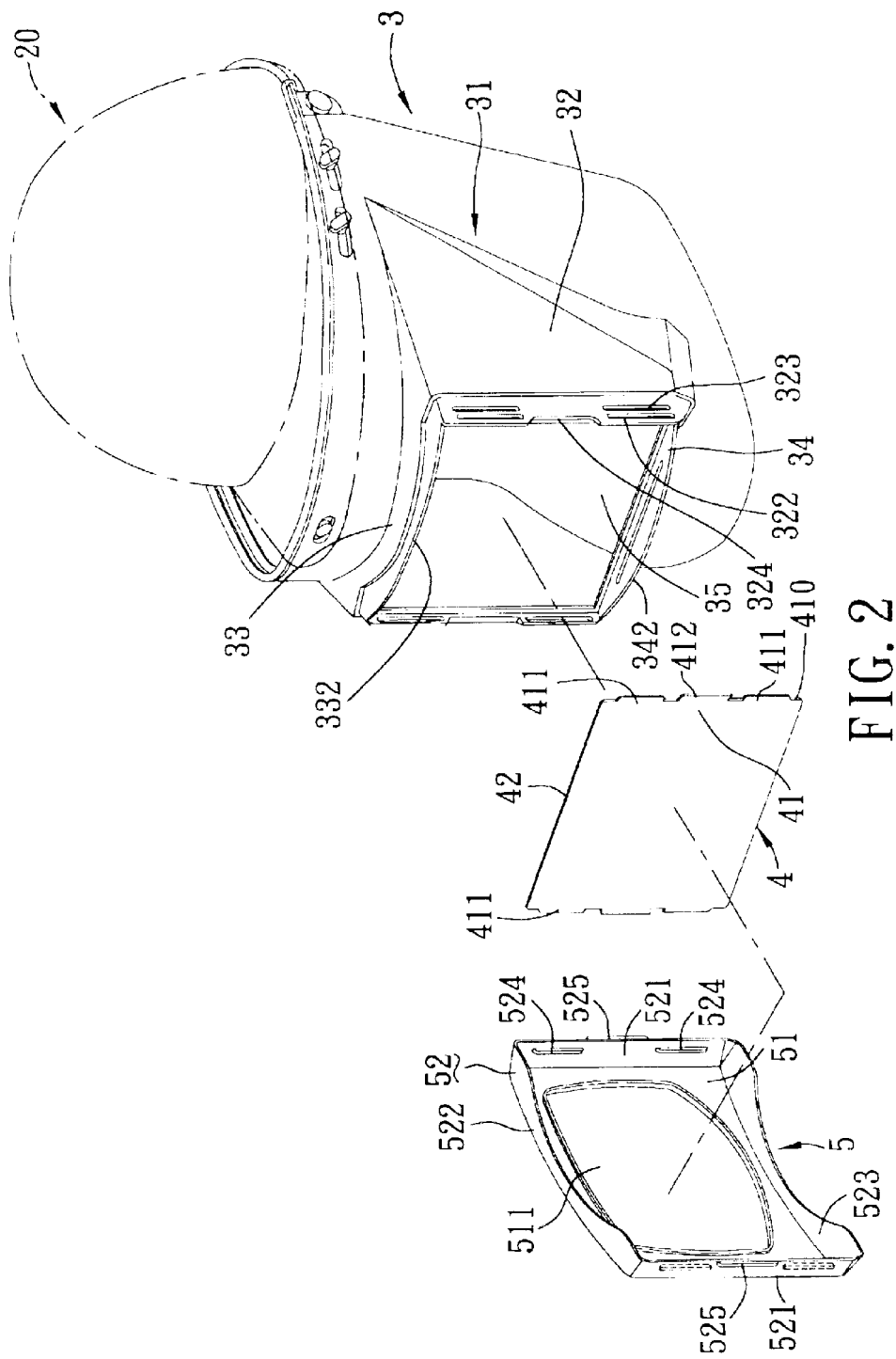
FIG. 2 is an exploded perspective view of the preferred embodiment of a protective mask according to the present invention when mounted on a helmet.
Figure 3:
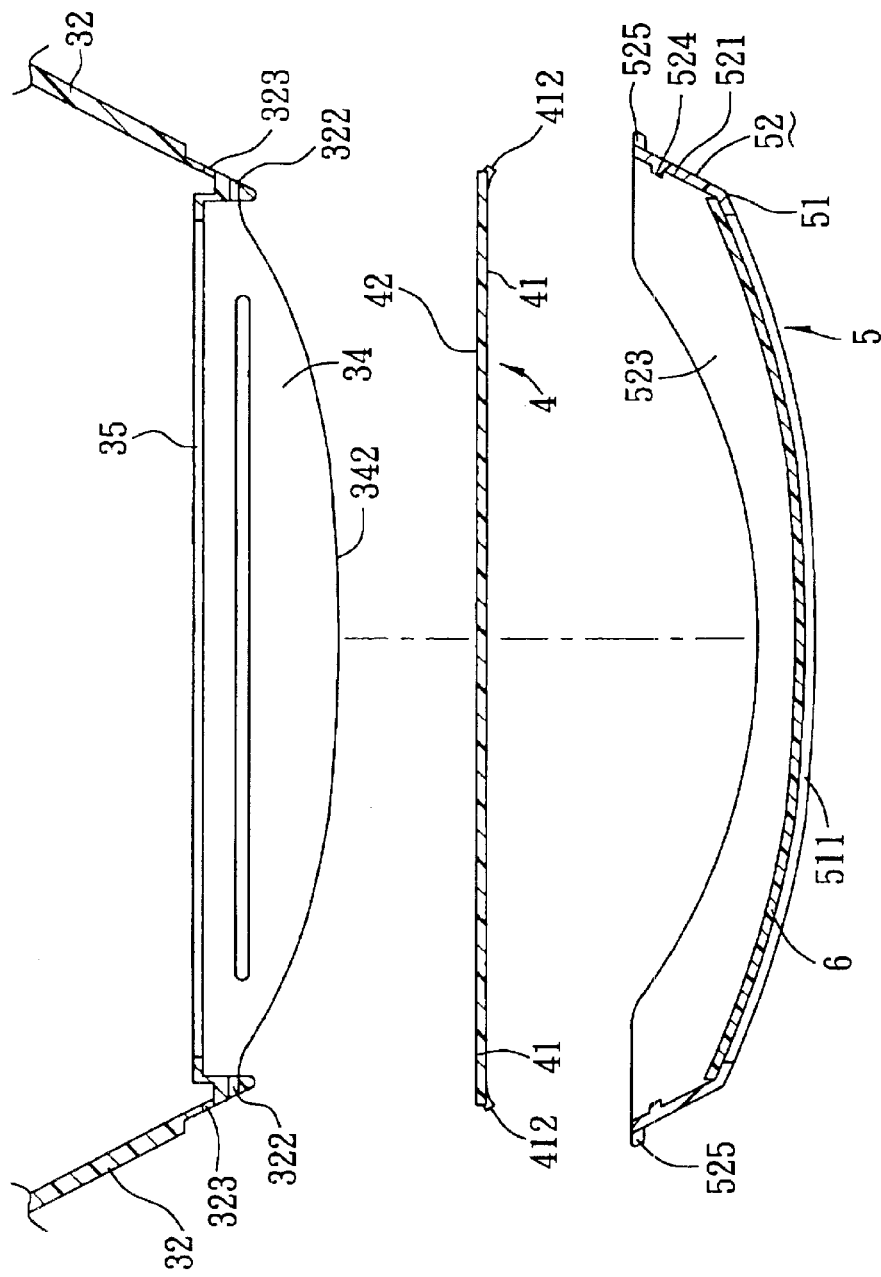
FIG. 3 is an exploded top sectional view of the preferred embodiment.
Figure 4:
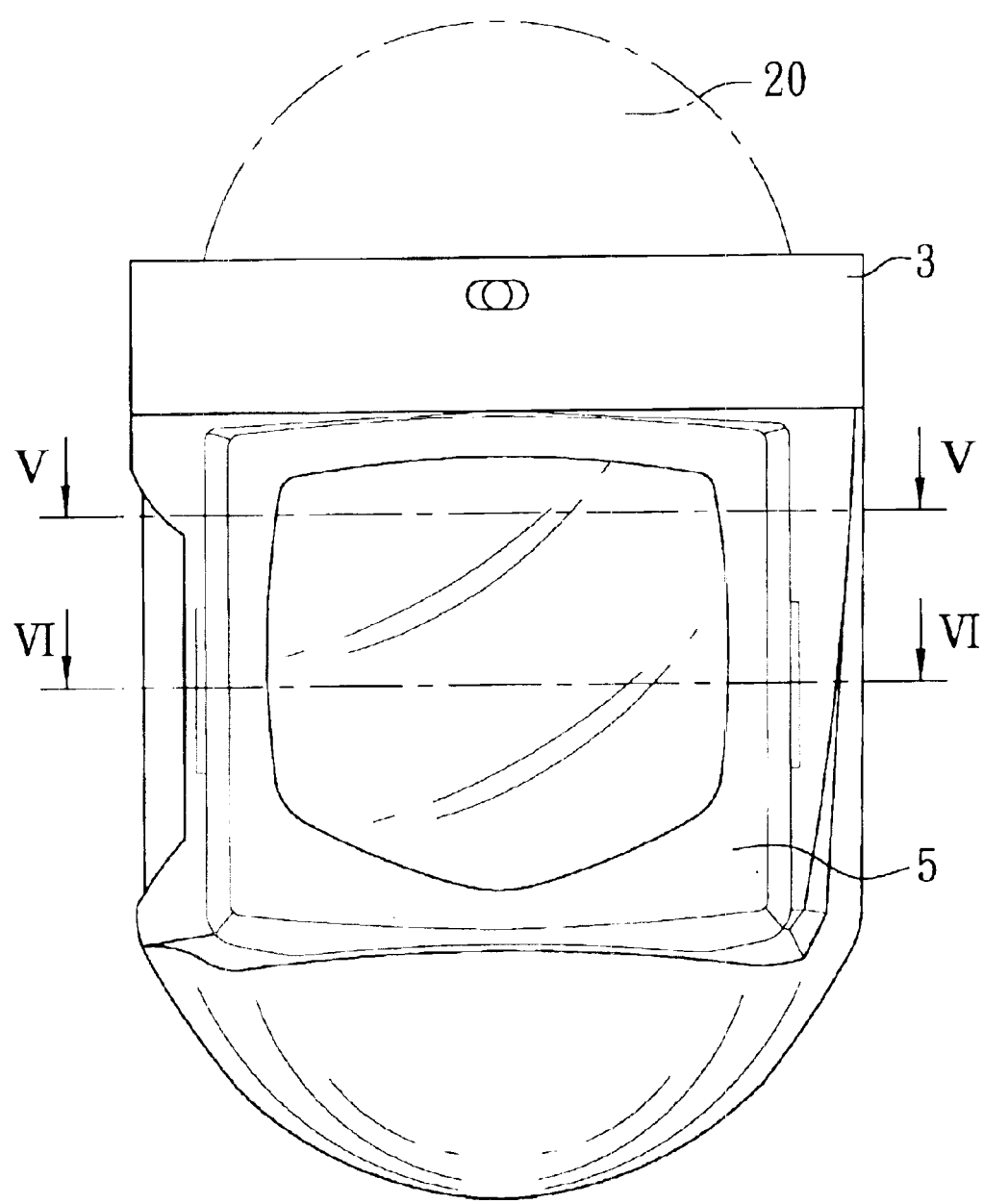
FIG. 4 is a front view of the preferred embodiment.

Referring to FIGS. 2, 3 and 4, the preferred embodiment of a protective mask according to the present invention is shown to include a mask body 3, a viewing member 4 (such as a tinted glass), and a shield-mounting member 5.

As illustrated, the mask body 3 is made from an anti-infrared plastic material, and is adapted to be attached detachably on a helmet 20. The mask body 3 is formed with a window frame 31 protruding therefrom in a transverse direction relative to the mask body 3. The window frame 31 defines a window 35.

The viewing member 4 is mounted detachably in the window frame 31 so as to cover the window 35, and permits vision therethrough.

Figure 5:
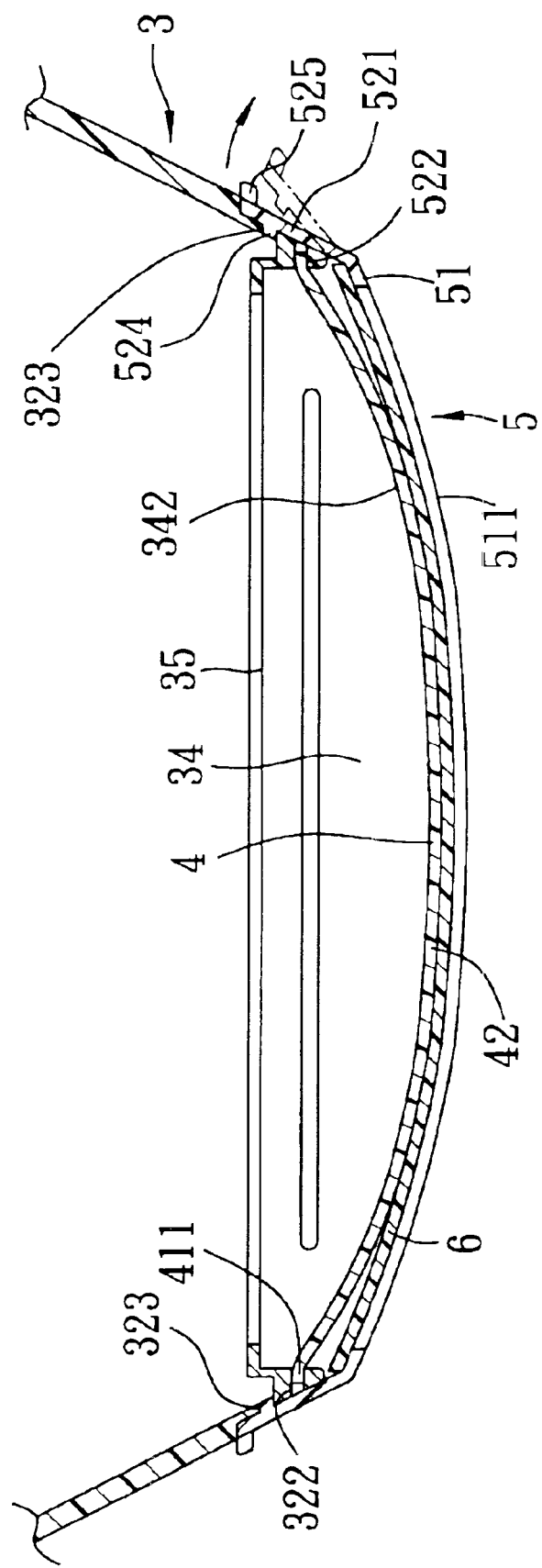
FIG. 5 is a sectional view of the preferred embodiment taken along lines V—V of FIG. 4.
Figure 6:
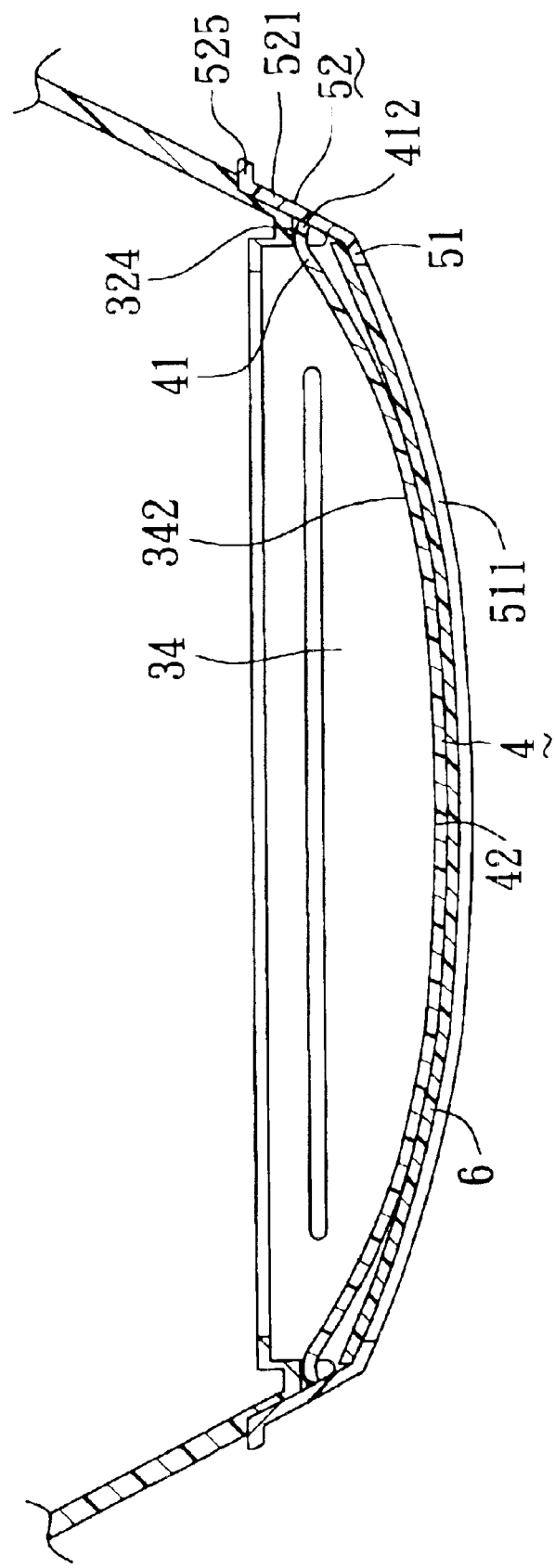
FIG. 6 is a sectional view of the preferred embodiment taken along lines VI—VI of FIG. 4.

The window frame 31 includes left and right frame parts 32, each of which is formed with two aligned first retaining slots 322. The viewing member 4 is in the form of a flexible plate 41 having opposite left and right sides 410 and left and right tongues 411 formed respectively on the left and right sides 410 and projecting respectively into the first retaining slots 322 in the left and right frame parts 32 (see FIGS. 5 and 6). The plate 41 is flexible in such a manner that bending of the left and right sides 410 of the plate 41 toward each other results in disengagement of the left and right tongues 411 from the first retaining slots 322. Each of the left and right frame parts 32 is preferably formed with a notch 324 between the first retaining slots 322. The plate 41 further has left and right detachment stubs 412 formed on the left and right sides 410 and respectively extending through the notches 324 in the left and right frame parts 32 (see FIG. 6). As such, when it is desired to remove the plate 41 from the window frame 31, the user can press the detachment stubs 412 of the plate 41 to move toward each other so as to bend the plate 41 and so as to facilitate disengagement of the tongues 411 from the first retaining slots 322.

The mask body 3 has upper and lower frame parts 33, 34 interconnecting and cooperating with the left and right frame parts 32 to define the window frame 31. The upper and lower frame parts 33, 34 respectively have curved upper and lower front ends 332, 342. The plate 41 is curved and is convex frontwardly, and has a concave rear face 42 abutting against the upper and lower front ends 332,342 of the upper and lower frame parts 33,34 (see FIGS. 5 and 6).

The shield-mounting member 5 is disposed frontwardly of the viewing member 4, and has a curved outer frame part 51 and a rectangular inner flange part 52 projecting rearwardly from a periphery of the outer frame part 51 in a direction transverse to the frame part 51. The outer frame part 51 defines a central opening 511. A curved transparent shielding plate 6 is sandwiched between the outer frame part 51 and the viewing member 4 for covering the central opening 511 and for protecting the viewing member 4. The inner flange part 52 has left and right sections 521, and upper and lower sections 522, 523 interconnecting and cooperating with the left and right section 521 to define a frame-receiving space thereamong. The window frame 31 of the mask body 3 is fitted into the frame-receiving space of the inner flange part 52 of the shield-mounting member 5.

Each of the left and right frame parts 32 of the window frame 31 is further formed with two aligned second retaining slots 323 that are disposed rearwardly of the first retaining slots 322. The left and right sections 521 of the flange part 52 of the shield-mounting member 5 have outer surfaces formed with left and right pull elements 525, and inner surfaces formed with left and right inner tongues 524 that extend respectively into the second retaining slots 323 in the left and right frame parts 32 (see FIGS. 5 and 6). As shown by the dotted lines in FIG. 5, the left and right pull elements 525 of the shield-mounting member 5 can be pulled outwardly away from the window frame 31 when it is desired to remove the shield-mounting frame 5 from the window frame 31.

With the provision of the window frame 31 on the mask body 3 and the curved plate 41 mounted detachably on the window frame 31, replacement of the viewing member 4 can be easily conducted, and the aforesaid disadvantage of the prior art can be overcome.

Figure 7:
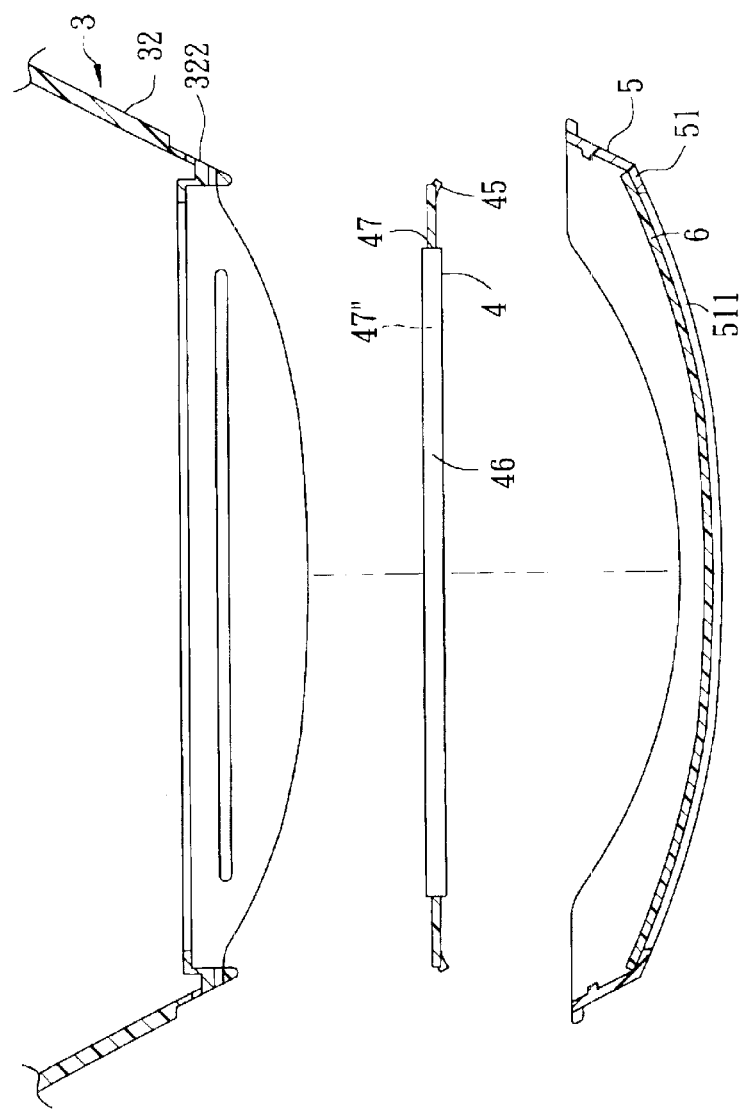
FIG. 7 is an exploded top sectional view of a modified preferred embodiment of the protective mask according to the present invention.

Referring to FIG. 7, a modified preferred embodiment of the protective mask according to the present invention is shown to have a construction similar to that of the previous embodiment. The main difference resides in that the viewing member 4 includes a mounting frame 47 defining a central opening 47", and having opposite left and right sides and left and right tongues 45 that are formed respectively on the left and right sides of the mounting frame 47 and that project respectively into the retaining slots 322 in the left and right frame parts 32 of the window frame A liquid crystal display panel 46 is mounted in the mounting frame 47 to cover the central opening 47".

With this invention thus explained, it is apparent that numerous modifications and variations can be made without departing from the scope and spirit of this invention. It is therefore intended that this invention be limited only as indicated in the appended claims.

I claim:

1. A protective mask comprising:
   a mask body made from an anti-infrared plastic material and formed with a window frame protruding therefrom in a transverse direction relative to said mask body, said window frame defining a window; and
   a viewing member mounted detachably in said window frame so as to cover said window and adapted to permit vision therethrough, wherein said window frame includes left and right frame parts, each of which is formed with a first retaining slot, said viewing member being in the form of a flexible plate having opposite left and right sides and left and right tongues formed respectively on said left and right sides and projecting respectively into said first retaining slots in said left and right frame parts, said plate being flexible in such a manner that bending of said left and right sides of said plate toward each other results in disengagement of said left and right tongues from said first retaining slots, further wherein said mask body has upper and lower frame parts interconnecting and cooperating with said left and right frame parts to define said window frame, said upper and lower frame parts respectively having curved upper and lower front ends, said plate being curved and being convex frontwardly and having a concave rear face abutting against said upper and lower front ends.

2. The protective mask as defined in claim 1, further comprising a shield-mounting member disposed frontwardly of said plate of said viewing member, and having a curved outer frame part and an inner flange part projecting rearwardly from a periphery of said outer frame part in a direction transverse to said outer frame part and defining a frame-receiving space, said window frame being fitted into said frame-receiving space.

3. The protective mask as defined in claim 2, wherein each of said left and right frame parts is further formed with a second retaining slot that is disposed rearwardly of said first retaining slot, said inner flange part of said shield-mounting frame having an inner surface formed with left and right inner tongues extending respectively into said second retaining slots in said left and right frame parts.

4. The protective mask as defined in claim 3, further comprising a curved transparent shielding plate that is sandwiched between said viewing member and said shield-mounting member.

5. The protective mask as defined in claim 1, wherein said window frame includes left and right frame parts, each of which is formed with a retaining slot, said viewing member including a mounting frame defining a central opening and having opposite left and right sides and left and right tongues formed respectively on said left and right sides of said mounting frame and projecting respectively into said retaining slots in said left and right frame parts, said protective mask further comprising a liquid crystal display panel mounted in said mounting frame to cover said central opening.

* * * * *